(12) United States Patent
Hung et al.

(10) Patent No.: US 7,419,826 B2
(45) Date of Patent: Sep. 2, 2008

(54) HUMAN SCHWANNOMA CELL LINE

(75) Inventors: Gene Hung, Arcadia, CA (US); Xiankui Li, Alhambra, CA (US)

(73) Assignee: House Ear Institute, Los Angeles, CA (US)

( * ) Notice: Subject to any disclaimer, the term of this patent is extended or adjusted under 35 U.S.C. 154(b) by 170 days.

(21) Appl. No.: 10/506,414

(22) PCT Filed: Mar. 3, 2003

(86) PCT No.: PCT/US03/06314

§ 371 (c)(1),
(2), (4) Date: Aug. 31, 2004

(87) PCT Pub. No.: WO03/073996

PCT Pub. Date: Sep. 12, 2003

(65) Prior Publication Data

US 2008/0051354 A1    Feb. 28, 2008

Related U.S. Application Data

(60) Provisional application No. 60/361,528, filed on Mar. 1, 2002.

(51) Int. Cl.
*C12N 5/08* (2006.01)

(52) U.S. Cl. .................. 435/368; 435/366; 435/325

(58) Field of Classification Search ............... None
See application file for complete search history.

(56) References Cited

U.S. PATENT DOCUMENTS 5,376,542 A * 12/1994 Schlegal ................ 435/6

OTHER PUBLICATIONS

Katakura et al, Methods in Cell Biology 57: 69-91, 1998.*
Munger et al, Virus Research 89: 213-228, 2002.*
Peden et al, Annual N.Y. Acad. Sci 605: 286-293, 1990.*
Rosenbaum et al, Neurobiology of Disease 5: 55-64, 1998.*
Zwarthoff, Pathol. Res. Pract. 192(7):647-57, 1996; Abstract only.*
Roque et al (Exp. Eye Res. 64: 519-527, 1997.*
Katakura et al, 1998, *of record.*
Li et al, Cancer Biotherapy & Radiopharm. 18(5): 829-840, 2003.*
Einheber et al, Journal of Cell Biology 129(2): 443-458, 1995.*
Bonetti et al, J. Neuropathol. Exp. Neurol. 59(1): 74-84, 2000.*
Steele et al, Carcinogenesis 21(1): 63-67, 2000.*
Drexler et al, Leukemia and Lymphoma 9:1-25, 1993.*
Hsu, in Tissue Culture Methods and Applications, Kruse and Patterson, Eds, 1973, Academic Press, NY, see abstract, p. 764.*
Tian et al, Physiol Genomics, 17: 170-182, 2004.*
Van Dyke et al, Cancer Genetics and Cytogenetics 241: 137-141, 2003.*
Zaslav et al, Amer J Medical Genetics 107: 174-176, 2002.*
Kunkel et al, Neuro-oncology 3(2): 82-88, 2001.*
Doering, L. (2001) "Components of cell and gene therapy for neurological disorders" *An Introduction to Molecular Medicine and Gene Therapy*, Chapter 9, pp. 203-233.
Muir, D. et al. (1990) "Schwann cell proliferation in vitro is under negative autocrine control" *The Journal of Cell Biology* 111:2663-2671.
Muir, D. et al. (1992) "Stromelysin generates a fibronectin fragment and inhibits Schwann cell proliferation" *The Journal of Cell Biology* 116:177-185.
Sherman, L. et al. (1999) "Overexpression of activated neu/erbB2 initiates immortalization and malignant transformation of immature Schwann cells in vitro" *Oncogene* 18:6692-6699.

* cited by examiner

*Primary Examiner*—Joseph Woitach
*Assistant Examiner*—Kevin K. Hill
(74) *Attorney, Agent, or Firm*—Knobbe Martens Olson, Bear LLP

(57) ABSTRACT

In a preferred embodiment, the present invention relates to a Schwannoma cell line derived from a Schwann tumor in a patient with Neurofibromatosis type 2 (NF2) and immortalized with HPV E6-E7 genes. The cell line has a unique splice site mutation of the NF2 gene. The immortalized cell line is non-tumorigenic but has altered growth properties such as higher proliferation rate and independence of Schwann cell growth factors. Methods of using this unique cell line for pharmacologic screening are disclosed.

8 Claims, 8 Drawing Sheets

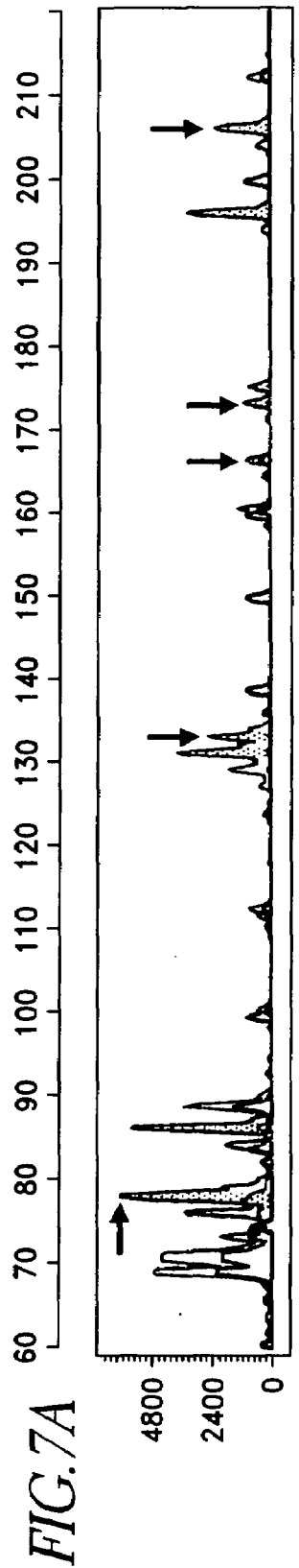
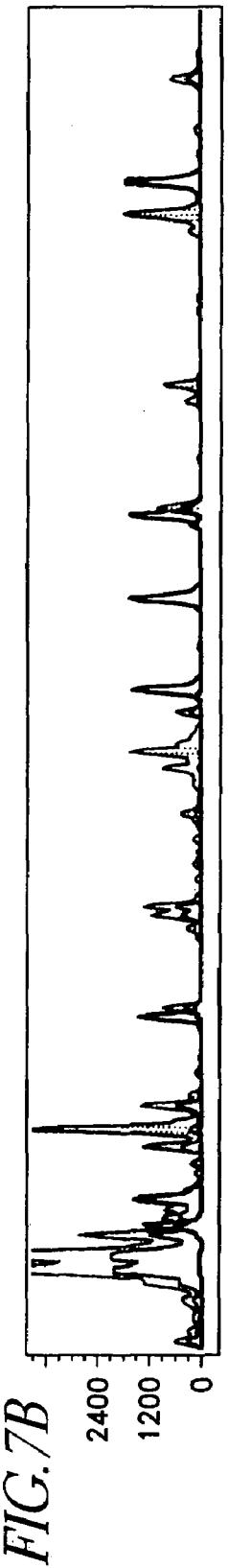
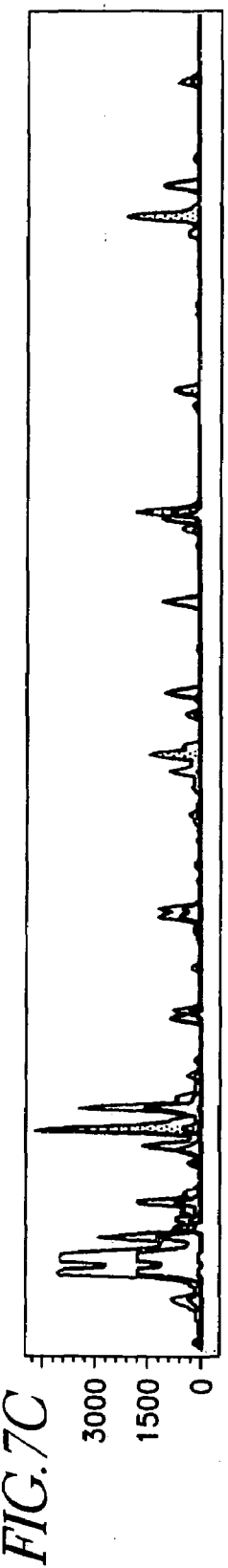
FIG. 7A
FIG. 7B
FIG. 7C

SEQUENCE LISTING

```
<160> NUMBER OF SEQ ID NOS: 4

<210> SEQ ID NO 1
<211> LENGTH: 459
<212> TYPE: DNA
<213> ORGANISM: HPV16

<400> SEQUENCE: 1
aatgttccag gacccacagg agcgacccat aaagttacca gatttatgca cagagctgca      60
aacaactata catgatataa tattagaatg tgtgtactgc aagcaacagt tactgcgacg     120
tgaggtatat gactttgctt ttcgggattt atgcatagta tatagagatg ggaatccata     180
tgcagtgtgt gataaatgtt taaagtttta ttctaaaatt agtgagtata gatattattg     240
ttatagtttg tatggaacaa cattagaaca gcaatacaac aaaccgttgt gtgatttgtt     300
gattaggtgt attaactgtc aaaagccact gtgtcctgaa gaaaagcaaa gacatctgga     360
caaaaagcaa agattccata atataagggg tcggtggacc ggtcgatgta tgtcttgttg     420
cagatcatca agaacacgta gagaaaccca gctgtaatc                            459

<210> SEQ ID NO 2
<211> LENGTH: 297
<212> TYPE: DNA
<213> ORGANISM: HPV16

<400> SEQUENCE: 2
```

```
atgcatggag atacacctac attgcatgaa tatatgttag atttgcaacc agagacaact          60
gatctctact gttatgagca attaaatgac agctcagagg aggaggatga aatagatggt         120
ccagctggac aagcagaacc ggacagagcc cattacaata ttgtaacctt ttgttgcaag         180
tgtgactcta cgcttcggtt gtgcgtacaa agcacacacg tagacatttg tactttggaa         240
gacctgttaa tgggcacact aggaattgtg tgccccatct gttctcagaa accatag            297

<210> SEQ ID NO 3
<211> LENGTH: 20
<212> TYPE: DNA
<213> ORGANISM: Artificial Sequence
<220> FEATURE:
<223> OTHER INFORMATION: sense primer

<400> SEQUENCE: 3
atggccgggg ccatcgcttc                                                      20

<210> SEQ ID NO 4
<211> LENGTH: 23
<212> TYPE: DNA
<213> ORGANISM: Artificial Sequence
<220> FEATURE:
<223> OTHER INFORMATION: antisense primer

<400> SEQUENCE: 4
gagctcttca aagaaggcca ctc                                                  23
```

HUMAN SCHWANNOMA CELL LINE

This application is a 371 of PCT/US03/06314 filed on Mar. 3, 2003 which claims benefit of the provisional application 60/361,528 filed on Mar. 1, 2002, the contents of which are incorporated by reference in their entirety.

BACKGROUND OF THE INVENTION

1. Field of the Invention

In one aspect, this invention relates to the establishment and characterization of a schwannoma cell line from a patient with neurofibromatosis 2. In another aspect this invention relates to methods of screening therapeutic treatments for neurofibromatosis 2.

2. Description of the Related Art

Neurofibromatosis 2 (NF2) is a genetic disorder characterized by the formation of multiple benign nervous system tumors, including schwannomas, meningiomas and ependymomas (Martuza, R. L. & tk tk Eldridge, R. 1988 *N Engl J Med* 318:684-688; Mulvihill, J. J. et al. 1990 *Ann Intern Med* 113:39-52; Evans, D. G. et al. 1992 *Q J Med* 84:603-618). These tumors are often benign with slow growth, but their location predominantly within the central nerve system (CNS) may have catastrophic effects on sensitive intracranial and intraspinal structures, thus, causing a high rate of morbidity and mortality. Affected individuals generally develop symptoms of eighth nerve dysfunction, including deafness (often bilateral) and balance disorder (Martuza, R. L. & Eldridge, R. 1988 *N Engl J Med* 318:684-688; Kanter, W. R. et al. 1980 *Neurology* 30:851-859). NF2 occurs with an incidence of approximately one in 40,000 live births where about 50% of cases reveal no family history and are likely due to new mutations (Evans, D. G. et al. 1992 *J Med Genet* 29:841-846).

Clinically, there are two subtypes in NF2 patients (Evans, D. G. et al. 1992 *J Med Genet* 29:841-846; Ruttledge, M. H. et al. 1996 *Am J Hum Genet* 59:331-342; Parry, D. M. et al. 1996 *Am J Hum Genet* 59:529-539; MacCollin, M. et al. 1995 *Ann Neurol* 38:554-555). Patients with the severe (Wishart) subtype usually have onset by 20 years of age, develop many CNS tumors in addition to bilateral vestibular schwannomas, and exhibit rapid clinical progression that may lead to death by the 3rd or 4th decade (Evans, D. G. et al. 1992 *J Med Genet* 29:847-852; Parry, D. M. et al. 1994 *Am J Med Genet* 52:450-461). On the other hand, patients with the mild (Gardner) subtype often do not develop symptoms until the 3rd decade, and have few tumors other than bilateral vestibular schwannomas and have a relatively benign clinical course (Evans, D. G. et al. 1992 *J Med Genet* 29:841-846; Parry, D. M. et al. 1994 *Am J Med Genet* 52:450-461).

The NF2 gene is located on chromosome 22q12 (Rouleau, G. A. et al. 1987 *Nature* 329:246-248). The genetic evidence from NF2 patients with schwannomas (Bijisma, E. K. et al. 1992 *Genes Chromosomes Cancer* 5:201-205), meningiomas (Dumanski, J. P. et al. 1987 *PNAS USA* 84:9275-9279), sporadic unilateral vestibular schwannomas (Parry, D. M. et al. 1994 *Am J Med Genet* 52:450-461) and mutated alleles, together with the loss of heterozygosity (LOH) for restriction fragment length polymorphism (RFLPs) on chromosome 22q, has suggested that the NF2 gene is a tumor suppressor gene.

Genotype-phenotype correlation analysis revealed that more severe disease (Wishart) tends to harbor NF2 mutations that result in premature protein termination due to frameshift mutations (deletions or insertions) or the presence of premature termination codon. In the patients with milder clinical disease (Gardner), the mutations are either missense mutations or due to not being found by ordinary mutation detection methods. It has been predicted that nonsense NF2 mutations could result in unstable truncated proteins whereas missense mutations might generate full-length proteins incapable of growth suppression (Gutmann, D. H. et al. 1998 *Hum Mol Genet* 7:335-345). In a recent report, differing growth rate were noted in culture when different sporadic vestibular schwannoma tumor tissues were cultured (Pelton, P. D. et al. 1998 *Oncogene* 17:2195-2209). Unfortunately, no NF2 gene mutation information was provided.

Currently, several biochemical experiments have also indicated that the NF2 protein directly interacts with plasma membrane molecules such as CD44, EBP50 or hNHE-RF/EBP50 and cytoskeleton molecules such as β II-spectrin (Sainio, M. et al. 1997 *J Cell Sci* 110:224-940). These findings suggest that the NF2 gene product may, like its homologous proteins ezrin, radixin and moesin (ERM), work as a linker between cell membrane and cytoskeleton. This linkage may block cytoplasmic growth signaling from the cell surface. However, a detailed pathway of how NF2 protein mediates the tumor suppression function is still unclear.

The establishment of an NF2-in vitro model is essential to elucidate the NF2 gene tumor 15 suppression function in Schwann cells and as the first step to test new therapeutic approaches. To date, no single cell line has been developed from NF2 tumor cells, and most studies were conducted either in yeast, mouse schwannoma cells or other non-Schwann human cells. There are three main reasons for this limited progress. First, human Schwann cells are difficult to obtain. Second, because of the lack of knowledge of Schwann cell growth factors, once the Schwann cells are obtained, they do not proliferate in culture. Third, there is the contamination of human fibroblast. Recently, we have developed a method for establishing short-term primary schwannoma cells in culture. These primary cultures can be enriched to greater than 99% pure and could be very useful for the study of genetic alterations and NF2 gene functions at the cellular and molecular level (Hung, G. et al. 1999 *Int J Oncology* 14:409-15).

SUMMARY OF THE INVENTION

Human Schwann or schwannoma cells are-essential for the study of NF2 tumorigenesis. In the past, researchers have had to rely on primary cultures of these cells for NF2 research. Such cultures have been of limited value, however, for the following reasons:

1) human Schwann cells are difficult to obtain, 2) very small numbers of cells can be obtained and cultured, 3) the cultures can be maintained for short periods of time and die quickly, and 4) fibroblasts often overgrow the culture.

The establishment of an NF2 cell line is therefore of significant value as it obviates the need for using primary cultures and enables scientists to perform studies that would not have been possible using primary cultures. The NF2 cell line can be used for studies including those aimed at 1) determining the function of NF2 gene in human Schwann cells and studying gene-gene interactions, in order to elucidate the molecular mechanisms involved in tumorigenesis and molecules that may be drug targets, 2) identifying genes whose expression is altered as a consequence of NF2 gene inactivation and this alteration, in order to identify those genes that determine the time of onset and severity of disease in different individuals, and 3) screening for drugs that reduce the growth rate of the tumors.

In this report, based on the primary cultures, we established and characterized for the first time a stable long-term human schwannoma cell line. The establishment of such a cell line provides a novel method to study tumor growth regulation conferred by NF2 and is envisioned to serve as a useful tool to test the gene-based therapeutic approaches in a disease model.

Therefore, in one aspect, the present invention relates to a stable, long-term human schwannoma cell line. In one preferred embodiment, the invention relates to the HEI-193 human schwannoma cell line on deposit as ATCC Accession # PTA4544.

In another aspect, the present invention relates to a method for establishing a stable long-term schwannoma cell line. The method comprises: isolating schwannoma cells from a schwannoma tumor by enzymatic digestion; plating the schwannoma cells in laminin-coated tissue culture dishes in a medium comprising insulin, progesterone, and heregulin; immortalizing the schwannoma cells by exposure to a retrovirus construct comprising the human papilloma virus E6-E7 genes and the Neor gene; and selecting immortal cells by resistance to neomycin. Preferably, the medium further comprises at least one additional component selected from the group consisting of bovine pituitary extract, transfenin, α-tocopherol, and forskolin.

In yet another aspect, the invention relates to a method for screening therapeutic treatments for neurofibromatosis 2. The screening method comprises: exposing schwannoma cells of a human schwannoma cell line of the present invention to a therapeutic treatment; and monitoring an index of schwannoma cell tumorigenesis. In preferred embodiments of the screening method, the index of tumorigenesis is monitored by an analysis selected from the group consisting of morphological changes, growth rate, immunohistochemical staining, NF2 gene analysis, chromosomal analysis, loss of heterozygosity analysis, and tumorigenicity in mice.

DETAILED DESCRIPTION OF THE PREFERRED EMBODIMENT

Figure 1A:
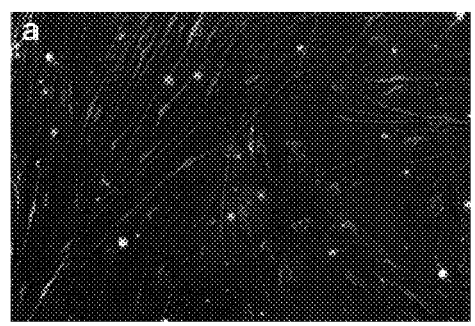
FIG. 1 shows the morphology of primary and immortalized schwannoma culture cells: (a) Primary schwannoma cells at Passage 1 from which HEI-193 cell line was derived. (b) A colony has formed 4 weeks after the viral transduction. The immortalized schwannoma cells are arranged in whorls, strands and sheaths pattern in confluent condition (c), 90%; and (d), 100%). (×100)
Figure 1B:
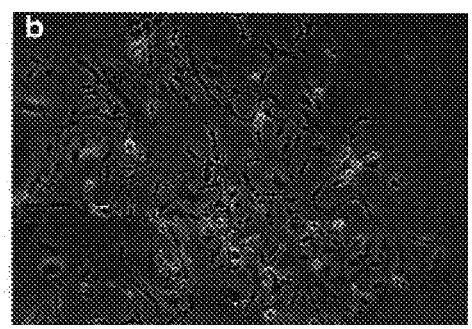
Figure 1C:
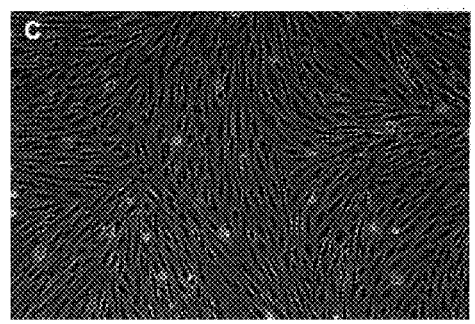
Figure 1D:
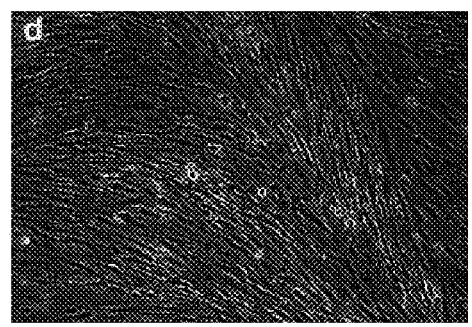
Figure 2A:
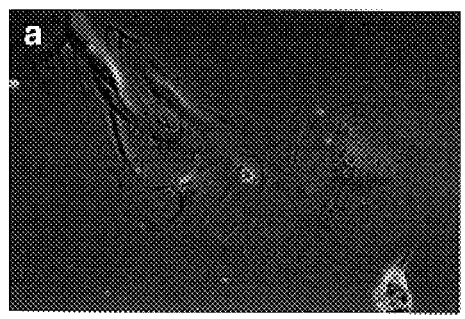
FIG. 2 shows the morphology change of HEI-193 cell line during the immortalization process. (a) shows more and more multinuclear syncytium cells could be seen after Passage 7. (b) The multinuclei as well as cytoskeleton elements were clearly displayed after Passage 14. (×200). (c) The cells displayed the heterogeneity with different shapes at Passage 9. (×100). (d) shows that the cells at Passage 15 displayed more homogenous shape. (×100).
Figure 2B:
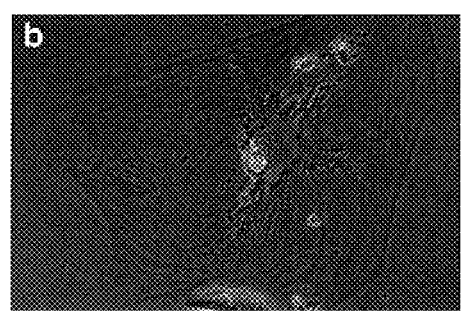
Figure 2C:
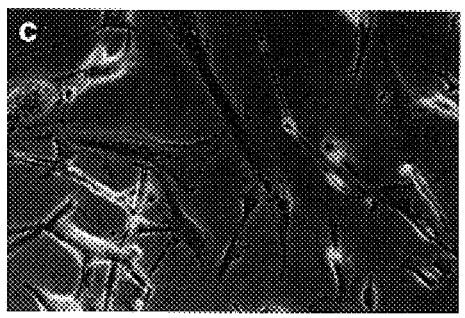
Figure 2D:
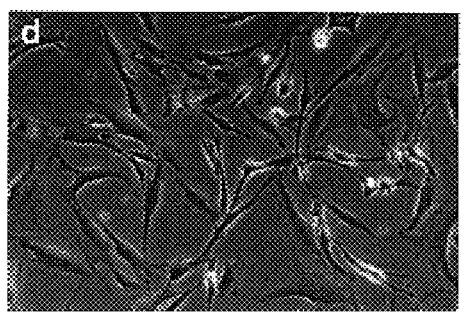

The present invention relates to an immortalized non-tumorigenic human schwannoma cell line free of other cell lines and containing an exogenous immortalizing gene. Methods of preparing this immortalized non-tumorigenic human schwannoma cell line, and methods of using this cell line are also included in the present invention.

Definitions

The term "cell line," as used herein, refers to individual cells, harvested cells, and cultures containing the cells, so long as they are derived from cells of the cell line referred to. A cell line is said to be "continuous," "immortal," or "stable" if the line remains viable over a prolonged time, typically at least about six months. To be considered a cell line, as used herein, the cells must remain viable for at least 40 passages.

A cell line is said to be "malignant" or "tumorigenic" if, when the cell line is injected into a host animal, the host animal develops tumors or cancers that are anaplastic, invasive, and/or metastatic. A "human" tumor is comprised of cells that have human chromosomes. Such tumors include those in a human patient, and tumors resulting from the introduction of a human malignant cell line into a non-human host animal if cells from such tumors have human chromosomes. A tumor is said to be "long-lasting" when the tumor persists in an animal for at least about one month.

As used in this application, the term "vector" refers to DNA or RNA vehicle, such as a plasmid, comprising nucleotide sequences enabling replication of the DNA or RNA in a suitable host cell. In this invention, a vector preferably includes a recombinant retrovirus containing oncogenes which are transcribed into mRNA and translated into proteins when the proviral sequence is expressed in the genetically modified target cell.

"Transfection" refers to the introduction of an exogenous nucleotide sequence, such as DNA vectors in the case of mammalian target cells, into a target cell whether or not any coding sequences are ultimately expressed. Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelopelcapsid-DNA complexes) and by biological infection by viruses such as recombinant viruses (Wolff, J. A. ed, *Gene Therapeutics*, Birkhauser, Boston, USA 1994). In the case of infection by retroviruses, the infecting retrovirus particles are absorbed by the target cells, resulting in reverse transcription of the retroviral RNA genome and integration of the resulting provirus into the cellular DNA. Genetic modification of the target cell is the indicia of successful transfection. "Genetically modified cells" refers to cells whose genotypes have changed as a result of cellular uptakes of exogenous nucleotide sequence by transfection. It will be appreciated that, as used herein, reference to "transfected cells" or "genetically modified cells" includes both the particular cell into which a vector or polynucleotide is introduced and progeny of that cell. "Primary cells" are cells that have been harvested from the tissue of an organism.

The present invention relates to a method for producing an immortalized human schwannoma cell line which comprises: providing primary human schwannoma cells in a culture; and transfecting the human schwannoma cells in the culture with an exogenous immortalizing gene so that the cell line is immortalized. Preferably the exogenous immortalizing gene is a human papilloma virus gene.

The primary Schwann or schwannoma cells to be immortalized by the method of the present invention can be from various donors and cell sources.

Human schwannoma cells are immortalized using the entire Human Papilloma virus (HPV) genome or portions thereof. The HPV DNA may be obtained from different strains of HPV which are associated with cancer. The HPV DNA may be obtained from different strains of HPV which are isolated from malignant or benign tumors taken from different tissues of humans. Examples of such strains of HPV include but are not limited to HPV-16, 18, 31, 33 and 35.

In one embodiment the cells are immortalized using the entire HPV genome from HPV-16, or the like. In another embodiment, the human schwannoma cells are immortalized using at least the E7 DNA portion of the genome or at least the E6 DNA portion of the genome or combinations thereof. In one embodiment a DNA sequence homologous or significantly homologous to the DNA sequence of E6 or E7 of HPV is used to immortalize human schwannoma cells. In another embodiment, the cells are immortalized using at least the E7 DNA portion in combination with the E6 DNA portion of the HPV-16 genome.

The preferred cell line was deposited under the Budapest Treaty on Jul. 11, 2002 with the American Type Culture Collection (10801 University Blvd., Manassas, Va.) as ATCC #PTA-4544. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strain is not to be construed as a license to practice the invention in contravention of the rights granted under the authority of any government in accordance with its patent laws.

I. Immortalized Cell Lines

The non-tumorigenic, stable, immortalized cell lines of the invention are derived from human Schwann or schwannoma cells. Immortalized cells are preferred over primary cells for use as a testing system because of greater reproducibility of results and less onerous preparation for use (once an immortalized cell line has been established). Immortalized cell lines, derived from human Schwann or schwannoma tissues serve as model toxicity systems for the respective tissues from which they were derived. Non-tumorigenic immortalized cells are particularly advantageous because of their greater similarty to normal tissue cells, and because they can be used for determining carcinogenic potential of test substances. The term non-tumorigenic is used to describe cells that do not form tumors when subcutaneously injected into a test animal, such as a mouse.

An immortalized cell line is prepared from cells obtained from a specific tissue of a single human donor. A homolog of that cell line is a second cell line prepared by the same method from the same tissue, but from a different donor. Different clonal isolates of a cell line are referred to as derivative cell lines.

Immortalized cells preferably retain expression of the enzymes that are involved in detoxification of xenobiotics, and their presence increases the authenticity of cellular toxicity testing system as a model for human tissues.

II. Expression Systems

The immortalizing genes can be transferred into the cell lines by transfection of plasmid DNA or by retroviral infection. The viral vector is preferably replication defective so that stable cell lines expressing immortalizing genes are obtained. Transfection of cells can occur through those methods commonly used, such as calcium or strontium phosphate treatment, microinjection, electroporation, or lipofection. For example, the cells may be infected with a molony-LTR driven promoter or a vaccine virus or lipofected with an adenovirus-promoter, HIV-promoter or CMV-promoter construct. The transfected DNA plasmid can contain a selectable marker gene or be co-transfected with a plasmid containing a selectable marker, and in some cases, the retroviral vector contains a selectable marker gene. Where one or more selectable markers are transferred into the cells along with the immortalizing gene, the cell populations containing the immortalizing gene can be identified and enriched by selecting for the marker or markers. Markers typically are antibiotic resistant to such antibiotics as tetracycline, hygromycin, neomycin, and the like.

In a preferred embodiment, the vector contains a bacterial neomycin resistance gene (Neo$^r$) as such a marker. Cells carrying Neo$^r$ may be selected by means known to those of ordinary skill in the art, such as the addition of 100-200 Ig/mL G418 to the growth medium. It will be readily apparent that other markers may be employed, and appropriate selections may be readily performed by those of ordinary skill in the art.

Retroviral vectors are the preferred vectors of this invention, though other viral vectors may be used, such as adenoviral vectors. Though adenoviral vectors have the advantage of not requiring dividing cells for transfection, they have a disadvantage in that they do not integrate into the genome, possibly making it more difficult to derive stable cell lines.

Adeno-associated viral (AAV) vectors might also be used but have the disadvantage of a smaller packaging limit than retroviral vectors.

The retroviral vector can be any that are known in the art. Retroviruses to be adapted for use in accordance with this invention can be derived from many avian or mammalian hosts. However, a requirement for use is that the virus be capable of infecting cells which are to be the recipients of the new genetic material (oncogene and/or desired gene) to be transduced using the retroviral vectors. Examples of retroviruses include avian retroviruses, such as avian erythroblastosis virus (AMV), avian leukosis virus (ALV), avian myeloblastosis virus (ABV), avian sarcoma virus. (ACV), Fujinami sarcoma virus (FuSV), spleen necrosis virus (SNV), and Rous sarcoma virus (RSV). Non-avian viruses include: bovine leukemia virus (BLV); feline retroviruses such as feline leukemia virus (FeLV) or feline sarcoma virus (FeSV); murine retroviruses such as murine leukemia virus (MuLV), mouse mammary tumor virus (MMTV), and murine sarcoma virus (MSV); rat sarcoma virus (RaSV); and primate retroviruses such as human T-cell lymphotropic viruses 1 and 2 (HTLV-1, 2), and simian sarcoma virus (SSV). Many other suitable retroviruses are known to those skilled in the art. A taxonomy of retroviruses is provided by Teich, in Weiss, et al. eds. *RNA Tumor Viruses*, $2^{nd}$ ed., Vol. 2 Cold Spring Harbor Laboratory, New York, pp. 1-16 (1985). For example, a retroviral vector may be constructed so as to lack one or more of the replication genes such as gag (group-specific antigen), pol (polymerase) or env (envelope) protein encoding genes. The resulting recombinant retrovirus would thus be capable of integration into the chromosomal DNA of an infected host cell, but once integrated, be incapable of replication to provide infective virus, unless the cell in which it is introduced contains another proviral insert encoding functionally active trans-acting viral proteins. Methods for producing infectious but replication deficient viruses are known in the art such as described in Mann, et al. 1983 *Cell* 33:153, and Miller, et al. 1986 *Mol Cell Biol* 6:2895.

The immortalizing genes, preferably oncogenes can be any that are known in the art. The oncogenes are preferably chosen according to the synergy amongst them in cellular transformation, and their ability to transform the target cells. Further, the large sizes of some oncogenes may affect their inclusion on the same vector. In order to provide transforming capability, the RNA or DNA constructs of the present invention incorporate at least two oncogenes, which can be derived from viral, cellular genomes, mammalian or avian chromosomal RNA or DNA. Partial lists of oncogenes are provided by Bishop, et a/., in: Weiss, et al. eds. *RNA Tumor Viruses*, Vol. 1, Cold Spring Harbor Laboratory, New York, pp. 1004-1005 (1984), and Watson et al., *Molecular Biology of the Gene*, 4th Ed., Vol II (Benjamin Cummings, Menlo Park, Calif., USA) p. 1037. Included are the known oncogenes such as jun, src, yes, abl, fps, fes, lrns, ros, kit, mos, rat, H-ras, K-ras, sis, SV40 T-antigen (SV40 T-Ag), HPV E6, HPV E7, Adenovirus EA, Her2/neu, C-erbB2, C-erB3, myc, myb, fos, ski and erbA. Many oncogene products have tymsine-specific protein kinase or serine/threonine protein kinase activity, or appear to be homologues of growth factors, growth factor receptors, or are nuclear proteins with unknown function. Many oncogenes can be obtained from public collections of deposited biological materials.

In a preferred embodiment the SV40 T-antigen, adenovirus E1A, or human papilloma virus E6 and/or E7 oncogenes are used.

Retroviral vectors capable of expressing multiple genes under the control of a promoter in eukaryotic cells are known in the art. For example, one method utilizes the ability of ribosome to reinitiate translation by a scanning mechanism after encountering a stop codon (Kozak, M., 1989 *J Biol Chem* 108:229-41). This has been exploited to develop retroviral vectors in-which two genes driven by the same promoter are efficiently expressed by being arrayed in close proximity (Levine, F., et al. 1991 *Gene* 108:167-74).

Transfection may be achieved by any of a variety of means described above and known to those of ordinary skill in the art including, but not limited to, retroviral infection. In general, plated cells may be transfected by infection with a suitable retrovirus, adenovirus, or adeno associated virus.

III. Utility of Cell Lines

The immortalized, non-tumorigenic, stable cell lines of the present invention are useful in the following respects.

(1) Identification of potential chemopreventive drugs. These cells are useful for screening chemicals suitable for the treatment of cancer and related diseases, by growing them in vitro in a medium containing the chemical to be tested and then, after a suitable period of exposure, determining whether and to what extent genotoxicity, DNA adduct formation, mutagenicity, cell transformation and/or cytotoxicity has occurred following exposure to a carcinogen, e.g., by trypan blue exclusion assay or related assays (Paterson, 1979 *Methods Enzymol* 58:141), or by growth assays such as colony formatting efficiency (MacDonald, et al. 1968 *Exp Cell Res* 50:417), all of which are standard techniques well known in the art. Once a potential anticarcinogenic agent is identified, it and the cells can be used in further studies, such as drug design.

(2) Programmed cell death. The cell lines are also used for identifying agents that induce programmed cell death or apoptosis, which may have an important impact on prevention of malignant transformation. Programmed cell death is assayed by DNA fragmentation or cell-surface antigen analysis.

(3) Studies of metabolism of carcinogens and other xenobiotics. Carcinogens and other xenobiotics may be added to the growth medium of these cells and then the appearance of metabolic products of these compounds may be monitored by techniques such as thin layer chromatography or high performance liquid chromatography and the like.

(4) Studies of DNA mutagenesis. Substances known or suspected to be mutagens, or precursors of mutagens, may be added to the growth medium of the cells and then mutations may be assayed, e.g., by detection of the appearance of drug resistant mutant cell colonies (Thompson, 1979 *Methods Enzymol* 58:308). Similarly, cell-mediated DNA mutagenesis may be studied by co-cultivating the cells of the present invention with cell types known or suspected to be capable of secreting mutagenic compounds (Hsu, et al. 1978 *PNAS USA* 75:2003).

Other standard methods well known in the art such as chromosome aberration and sister chromatic exchange induction in Chinese hamster ovary cells (Galloway, et al. 1985 *Environ Mutagen* 7:1) or mouse lymphoma cell mutagenesis assays (Myhr, et al. 1985 *Prog in Mut Res* 5:555-568) can, of course, also be used for testing mutagenicity.

(5) Studies of chromosome damaging agents. Substances known or suspected to cause chromosomal damage may be added to the culture medium of the cell lines of the present invention, and then the extent of chromosomal damage may be measured by techniques such as measurement of the frequency of sister chromatic exchange (Latt, et al. 1984 In: Tice, R. R. & Hollaender, A. *Sister Chromatic Exchanges*, New York: Plenum Press, pp. 11).

(6) Studies of malignant transformation. Chemical, physical and viral agents, and transferred genes including oncogenes, mutant tumor suppressor genes, and high molecular weight genomic DNA from-tumors are introduced into cells and malignant transformation is determined using standard assays such as anchorage independent growth or tumor formation in athymic nude mice.

(7) Screening for potential chemotherapeutic agents. Cells altered by transfer of oncogenes or chemical carcinogens (as in paragraph 6 above) are used to screen for chemotherapeutic agents by tests which examine reversion of the transformed phenotype of cells by reduction of agar growth or reduced tumor formation in nude mice.

(8) Studies of cellular biochemisty. For example, changes in intracellular pH and calcium levels are correlated with cell growth and action of exogenous agents including, but not limited to, those described in paragraphs 1 through 7 above. To study intracellular pH and calcium levels, cells in suitable culture vessels are exposed to fluorescent indicator dyes and then fluorescence emissions are detected with a fluorescence spectrophotometer (Grynkiewicz, et al. 1985 *J Biol Chem* 260:3440-3450).

(9) Studies of cellular responses to growth factors and production of growth factors. The cells may be used to identify and purify growth factors important for growth and differentiation of human Schwann or schwannoma cells.

(10) Studies of intracellular communication, e.g., by dye scrape loading assays. To determine whether the cells growing in vitro have the ability to communicate via gap junctions, the cultures may be scraped, e.g., with a scalpel in the presence of a fluorescent dye in the growth medium. Cells at the edge of the wound are mechanically disrupted and therefore take up dye; whether intercellular communication has occurred may be ascertained by determining whether cells distant from the wound also contain dye.

(11) Characterization of cell surface antigens. The cells are incubated with an antibody against the cell surface antigen of interest, and then reacted with a second antibody which is conjugated to a fluorescent dye. The cells are then evaluated using a fluorescence activated cell sorter to determine whether they are fluorescent and therefore possess the cell surface antigen.

(12) Hybrid studies for identification of tumor suppressor activity. To determine whether these cell lines contain tumor suppressor genes, they are fused to malignant tumor cells. The presence of tumor suppressor genes is indicated by loss of malignancy, e.g., as detected by loss of ability to form tumors in athymic nude mice, in the hybrid cells. See Stanbridge, et al. 1982 Science 215:252-259.

(13) Identification of novel genes. Novel genes, including transforming genes in naturally occurring cancers described in paragraph 6 above, growth factor genes as described in paragraph 9 above, tumor suppressor genes as described in paragraph 12 above, using standard molecular biological techniques (Davis, et al. 1986 *Methods in Molecular Biology*, New York: Elsevier) and techniques such as cDNA subtraction cloning and the like. These genes or their derivatives can be used in gene therapy.

(14) Study of neurodegeneration. The cell lines of the present invention are envisioned to be useful in studies of neurodegeneration, e.g., demyelination, paralysis, neuropathy, and the like. Various agents may be screened for their ability to prevent or treat demyelination, paralysis, and neuropathy, as well as for their ability to induce nerve regeneration, and axonal outgrowth. The cell lines of the present invention are also envisioned in treating neurodegenerafion by implanting the cells at the site of such neurodegeneration.

Of course, kits for screening various agents, e.g., carcinogenic or anfineoplasfic agents and for any other usage as described herein, are easily assembled, comprising container (s) containing the cell line(s) of the present invention, media for propagating cells, and reagents and/or apparatus for detecting morphological, physiological and/or genetic responses in the cell lines. Other components routinely found in such kits may also be included together with instructions for performing the test.

The following Examples are presented to illustrate some aspects of the invention, and are not to be construed as limiting the scope of the invention.

Patient Material. The patient was a 56-year-old male with a NF2 tumor of the ears. Neither his parents nor siblings have any features suggestive of NF2. His only 27-year-old daughter does not have any certain features of NF2. He had bilateral vestibular schwannomas and right optic nerve tumor acoustic at age of 39. When he was 40, he underwent posterior fossa craniectomy for removal of the right vestibular schwannoma, which left him deaf on that side. Subsequently, he underwent the surgical removal of a meningioma which included exenteration of the globe. Two years ago, the patient underwent the surgical removal of the left vestibular schwannoma. After obtaining informed consent for genetic studies, blood and tumor tissue were obtained from the patient. No adjuvant chemotherapy or radiation had been given prior to collection of tumor material.

Tumor Cell Culture Establishment. Primary Culture: The detailed procedure for establishing primary vestibular schwannoma culture was described previously (U, R. H. 1998 *Methods in Cel Biol* 57:167-186). In brief, vestibular schwannoma tumor tissue from the patient was transferred to the laboratory and cut to 2 mm$^3$ in size and digested with 10 mg/ml collagenase/dispase (Boehringer Mannheim) at 37° C. with 5% $CO_2$ for one hour. The digested tumor cells were washed and transferred twice during the first 48 hours, and then plated in 100-mm laminin-coated dishes with modified D-MEM/F12 medium (Gibco/BRL) supplemented with insulin 10 ℓg/ml (Sigma), progesterone 3×10$^{-8}$ M (Sigma), heregulin 10 nM (Genentech), bovine pituitary extract 3 ℓg/ml (Gibco/BRL), transferrin 10 ℓg/ml (Sigma), α-tocopherol 5 ℓg/ml (Sigma) and forskolin 5 ℓM (Sigma).

Immortalization of primary culture. At the first passage, 5×10$^5$ cells were plated in 60-mm laminin-coated plate, and fetal bovine serum (FBS) (HyClone, Utah) was added to 10%. Twenty-four hours after the serum was added, 1×10$^7$ of retrovirus construct pLXSN (Clontech, CA, cat # K1060-B; GenBank Accession # M28248) containing human papilloma virus (HPV) E6-E7 genes (SEQ. ID NO: 1 and SEQ. ID NO: 2) and Neor gene were added to the culture medium (Miller, A. D. & Rosman, G. J. 1989 *Biotechniques* 7:980-90; Galloway, D. A. et al. 1994 *Cold Spring Harb Syrnp Quant Biol* 59:297-306; Rhim, J. S. et al. 1998 *Carcinogenesis* 19:673-81; Bright, R K. et al. 1997 *Cancer Res* 57:995-1002). The culture cells were then maintained at 37° C. with 5% $CO_2$. Once colonies were formed, G418 (Gibco/BRL) was added to the final concentration of 0.4 ℓg/ml for neomycin resistance selection. After 8-10 days and several changes of the culture medium, the drug resistant cells were recorded as Passage 0. The cell line was designated HEI-193 (for House Ear Institute).

Proliferation Assays. Proliferation of the cells was monitored by visualizing 5-bromo-2'deoxyuridine (BrdU) incorporation (Porstmann, T. et al. 1985 *J Immunol Methods* 82:169-179) using colorimetric immunoassay kit (Boehringer Mannheim), according to the manufacturer's recommendation.

Immunohistochemical characterization. The cultured tumor cells were plated in laminin-coated chamber slides. Forty-eight hours later, plated cells were fixed in methanol/ethanol (1:1) at −20° C. for 15 minutes. The slides were then washed three times with phosphate-buffered saline (PBS) and blocked with 10% normal goat serum (NGS) in PBS for 20 min at room temperature. Cells were incubated for one hour with primary antibody—S100 (1:500, Dako Corp., Carpenteria, Calif.) which is a marker specific for Schwann cells among peripheral nerve cell types. After washing three times with PBS, secondary fluorescein-isothiocyanate (FITC)-conjugated goat anti-rabbit antibody (1:15, Dako Corp.) was added and incubated for 30 min at room temperature. After three washes with PBS, the slides were covered with antifade/pipidien iodine or regular permount and viewed under a Zeiss fluorescent microscope (Zeiss, Germany).

RT-PCR and DNA Setiuencin. To detect and compare NF2 gene messages from HEI-193 cells, patient tumor tissue and patient blood, RNA was prepared by using TRIzol solution (Gibco/BRL) according to the manufacturer's protocols. Reverse-transcription polymerase chain reactions (RT-PCR) were carried out using an RT-PCR kit (Stratagene), according to the manufacturer's procedure. The primers used to amplify the entire NF2 coding sequence from the RNA-derived cDNAs were: Sense Primer 5'-ATGGCCGGGGC-CATCGCTTC-3' (SEQ ID NO: 3), Antisense Primer 5'-GAGCTCTTCAAAGMGGCCACTC-3' (SEQ ID NO: 4). The PCR profile was as follows: 94° C. for 2 min, 68° C. for 3 min for 30 cycles. The final extension was added at 68° C. for 10 min before storage at 4° C. The PCR products from tissue, blood, and HEI-193 cells were loaded onto a 1% of agarose gel for electrophoresis. For direct DNA sequencing of the PCR products, seven different primers were synthesized for sequencing the entire coding region (Hung, G. et al. 1999 *Int J Oncogene* 14:409-15). The sequencing reaction procedure was according to the manufacturer's instructions (ABI Big-Dye Terminator Perkin-Elmer, Calif.), and the reactions were run and analyzed by an automated Genetic Analyzer ABI 310 system.

Karyotyping Analysis. Karyotyping was performed by Dr. Hukku at Children's hospital of Michigan at Detroit, when HEI-193 cell line at Passage 17. In brief, the logarithmic phase of cell growth was arrested with 0.06 lg/ml of colcemid for 1 hour, and then trypsinized and treated with 0.0375 M of KCl for 9 min. The cells were fixed with a mixture of methanol/acetic acid at a 3:1 ratio (Peterson, W. D. Jr. et al. 1979 *Methods Enzymol* 58:164-78). Cell suspensions in the fixatives were dropped onto cold wet glass slides. The slides were air dried and stained with 4% Giemsa solution. Chromosomes were examined and counted to establish the ploidy distribution and constitutional aberrations. For trypsin Giemsa banding of chromosomes, the slides were aged at 60° C. on a slide warmer for 18 hours, trypsinized for 3 seconds, stained with Giemsa stain for 11 min (Hukku, B. & Rhim J. S. 1993 *Cancer Genet Cytogenet* 68:22-31), washed, dried and then mounted in permount. The well-banded metaphases were karyotyped using AKSII image analysis system.

Loss of heterozygosity (LOH) analysis. For loss of heterozygosiy analysis, genomic DNAs were extracted from the corresponding tumor tissue, blood and cultured HEI-193 cells by using TRIzol solution (Gibco/BRL). LOH analysis was performed using five selected microsatellite markers either flanking or within the NF2 gene: CRYB2 (centromeric) (Marineau, C. & Rouleau G. A. 1992 *Nucleic Acids Res* 20:1430), D22S275 (centromeric), NF2CA3 (intragenic) (Boum, D. & Strachan T. 1995 *Hum Genet* 95:712), D22S268 (telomeric) (Marineau, C. et al. 1993 *Hum Mol Genet* 2:336) and D22S430 (telomeric) (Sainz, J. et al. 1993 *Hum Mol Genet* 2:2203; Evans, D. G. et al. 1997 *J Neurol Neurosurg Psychiatry* 62:3616). These five markers were amplified from tumor tissue, cultured cells or blood DNAs and analyzed for their heterozygosities. One of each primer pair was fluorescently labeled with either one of three dye phosphoramidites—FAM, TET or HEX (ABI, Foster City). PCR amplifications and electrophoresis were performed as described previously (Rosenbaum, C. et al. 1998 *Neurobiol Dis* 5:55-64). The amplified markers were separated on an automated Genetic Analyzer ABI310.

Inoculation of schwannoma cells in mice. Three of each SCID (Severe Combined Immunodeficient) mice and nude mice were used in this study. 6×10$^6$ of HEI-193 cells were subcutaneously injected into right flank area of the mice. The mice were followed up to 8 weeks for signs of tumor growth.

EXAMPLES

Example 1

Cell Line Establishment

Vestibular schwannoma tissue, which has been characterized containing an unique NF2 mutation (1575-1 g to a) at Exon 15 splicing site from a 56-year-old NF2 patient (Rosenbaum, C. et al. 1998 *Neurobiol Dis* 5:5564), was used for isolating the schwannoma cells. At the first passage, the cells were immortalized with a retrovirus construct pLXSN encoding HPV E6-E7 and Neol. After 8-10 days of G418 selection, characterization of the cell line was performed. The cell line was designated HEI-193 for House Ear Institute and has been propagated in culture for over 40 passages.

Indices of Schwannoma Cell Tumorigenesis

Example 2

Momhology Changes

Four to six weeks post retroviral transduction of the primary culture, a small population of short bipolar, spindle shape cells have formed colonies mixed in the untransduced schwannoma cells with long process shape (FIG. 1, a and b). Interestingly, only during the first 7 passages, when in confluence condition the cells were growing arranged like in vivo which formed whorls, strands and sheaths pattern (FIG. 1, c and d). After Passage 7, the cultured cells started to show increasing heterogeneity in morphology and decreased proliferation rate. More and more multinuclear syncytium cells could be seen in the culture (FIG. 2, a and b). It is interesting to note that in some of the syncytia the cytoskeleton elements were distinctly displayed (FIG. 2, a and b). At Passage 14 the culture reached its peak of crisis during which approximately half of cells began to die. This phenomena lasted about two weeks at which time a distinguishable small population of the culture cells with even shorter spindle shape survived and grew well (FIG. 2, c and d).

Example 3

Growth Rate

Figure 3:
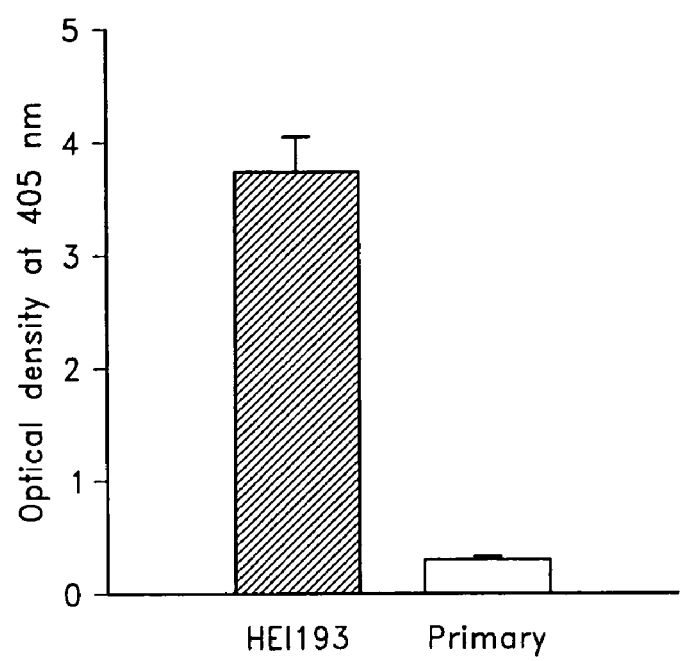
FIG. 3 shows a comparison of proliferation rates of HEI-193 cells and its parental primary culture cells.

The transduced cells have dramatic increase in growth rate. Proliferation rate of HEI-193 cells was measured by using colorimetric immunoassay (Porstmann, T. et al. 1985 *J Immunol Methods* 82:169-79). The BrdU incorporation in HEI-193 cells at Passage 17 was 13 times (3.730/0.29 of $OD_{405}$) more than that in primary cells (FIG. 3).

Example 4

Immunohistochemical Staining

Figure 4A:
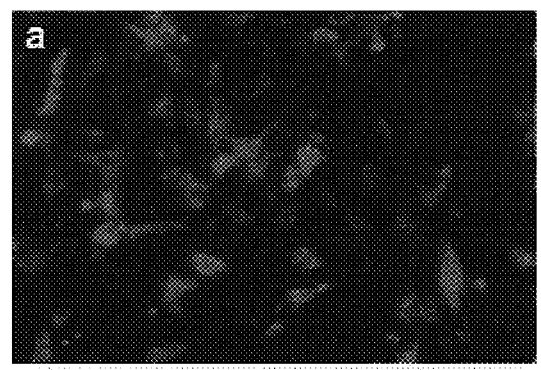
FIG. 4 illustrates immunohistochemical staining of the culture for Schwann cell specific antibody S100. Different S100 expressions were observed of the culture cells at Passage 7 (a) and Passage 17 (b). (×100).
Figure 4B:
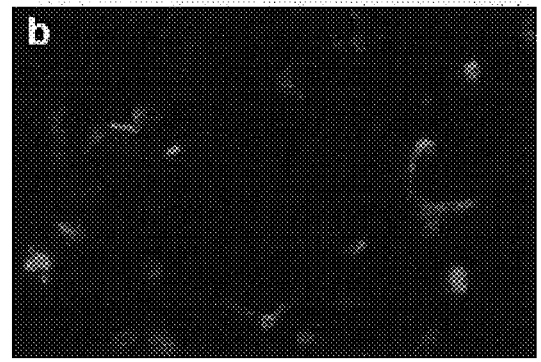

To assure that the cells purified and expanded from schwannomas were Schwann cells, the characteristics of the primary culture cells were stained with Schwann cells marker S100 (Hung, G. et al. 1999 *Int J Oncogene* 14:409-15). Greater than 99% of schwannoma cells were used for immortalization. The culture cells at every other passage were stained for Schwann cell specific antibody S100 which shown increasing heterogeneous expression during immortalization (FIG. 4).

Example 5

NF2 Gene Analysis

Figure 5:
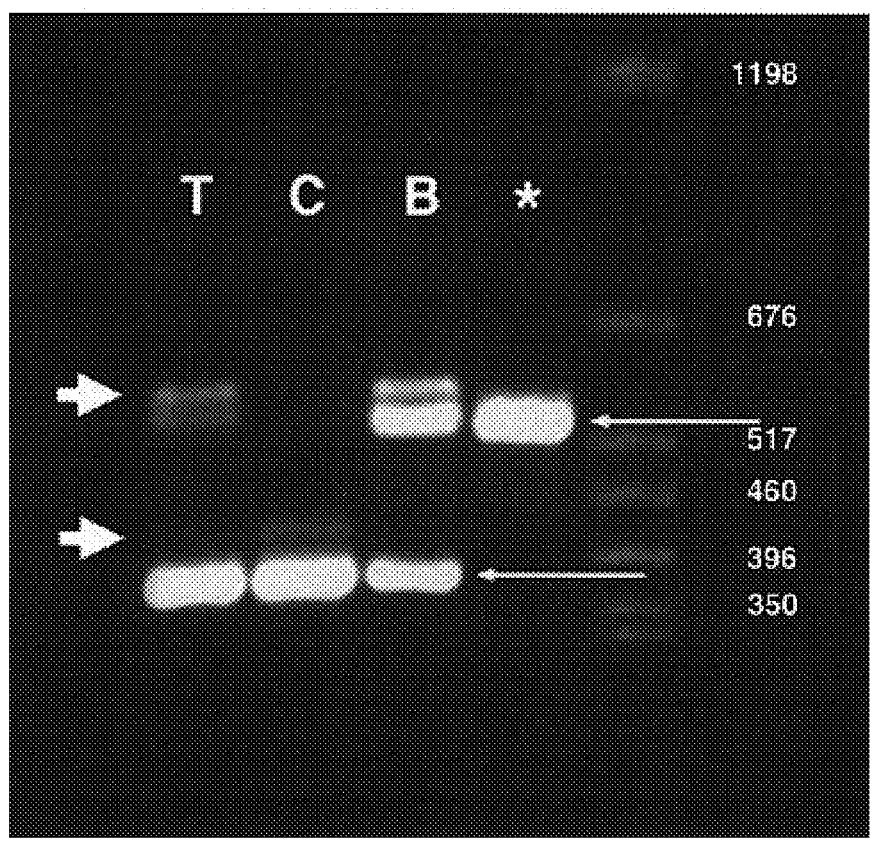
FIG. 5 shows NF2 gene analysis HEI-193 cells. RT-PCR products of NF2 gene from tumor tissue (T), HEI-193 cultured cells (C), the patient's blood (B) and (*) the positive control NF2 cDNA were loaded onto 1% agarose gel for electrophoresis. The far right lane and the number the column is molecular size marker. It is noted that except the truncated NF2 transcripts were detected (lower bends), no wild-type NF2 message can be detected from the cultured cells. Both wild type and mutated transcripts were observed in RNA extracted from tumor tissue and blood samples. The big arrowheads show PCR products containing alternative splicing with Exon 16. The small arrowheads point out the PCR products without Exon 16.

To detect and compare NF2 messages from the cultured cells, patient tumor tissue and patient blood, RT-PCR products of 3' end of NF2 gene from the same patient were electrophoresed on an agarose gel (FIG. 5). Both PCR products from tissue and blood showed the wild-type (WT) and mutated NF2 gene messages. PCR products from tumor tissue showed more than 90% of the products were the truncated form, and less 10% of WT NF2 transcript from normal stroma tissues. In blood, the wild type/mutant PCR products ratio is about 50:50. In contrast, the PCR product from the cultured cells contained only the mutated NF2 messages. This further confirms that HEI-193 cell line has no contamination of other non-tumor cells. By direct DNA sequencing, the PCR products from both tumor tissue and cells of HEI-193 cell line showed the same splice site at the acceptor site of Exon 15, suggesting HEI-193 retained the patient schwannoma origin.

Example 6

Chromosomal Analysis

Figure 6:
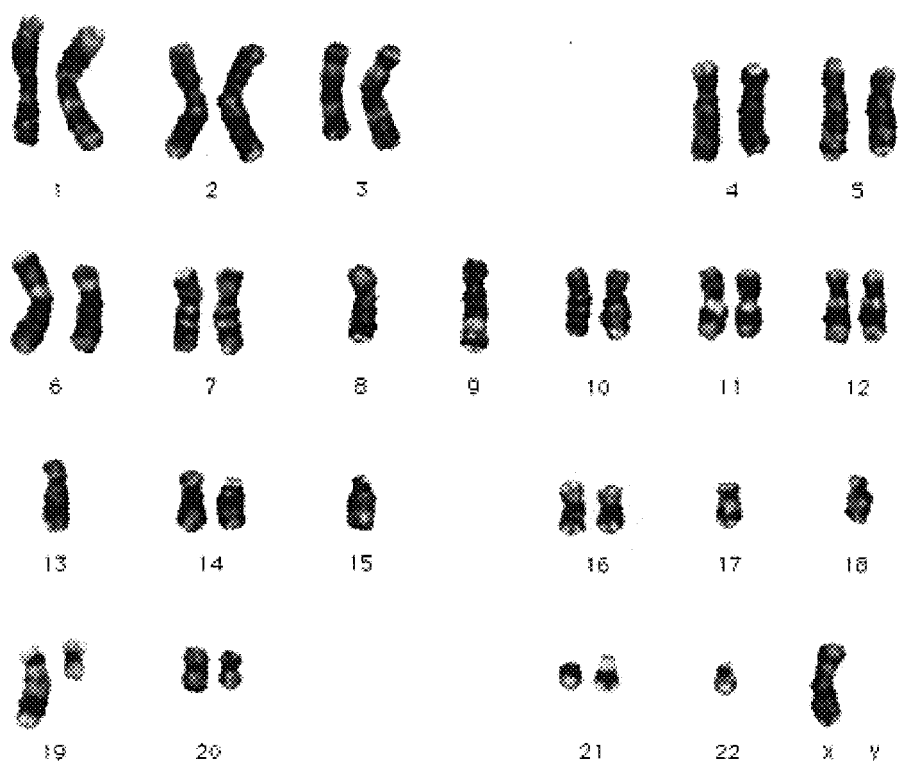
FIG. 6 shows a karyotype of metaphase cell from HEI-193 cell line. It has been observed that one complete copy of chromosome 8, 13, 15, 17, 18, 22 and Y has been lost in majority of metaphases.

According to chromosome count, the HEI-193 cell line is hypodiploid human male (XO), with most chromosome counts in the 35-41 range. The model number was 37. There were about 75% hypodiploid and 25% hypotetraploid metaphases observed. The composite karyotype was: 35-41, XO—(8, 9, 9, 13, 13, 14, 15, 17, 18, 19, 20 and 22)+[t (9, 13)(q10, q10)=M1, add (9)(q33)=M2, add (14)(q10) t(14;20) (q10,p10)=M3, t(15;?)(q10;?)=M4, der (19) t(13,19)(q12, q13)=M5]—(6, 10, 15, 17, 21) X15. There was loss of one complete copy of chromosome 8, 17, 18 and 22 in majority of metaphases (FIG. 6).

Example 7

Loss of Heterozygosify Analysis

Figure 7D:
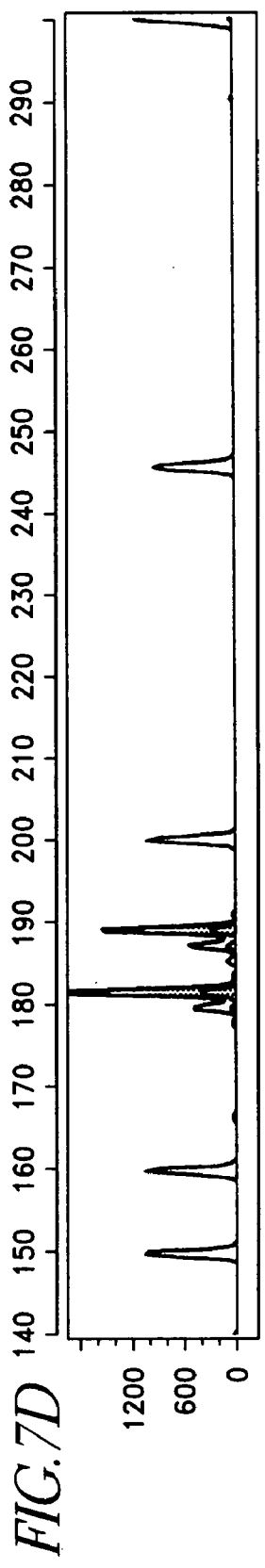
FIG. 7 shows LOH analysis of blood, tumor tissue and HEI-193 cell line. The electrophoregrams show 5 microsatellite markers [D22S430 (Peak 79, 87), NF2CA3 (Peak 131, 133), D22S275 (Peak 161, 167), CRYB (Peak 173, 175) and D22S268 (Peak 196, 206)]. Comparing with the electrophoregram display from blood DNA (a), LOH were observed in DNAs from both (b), tumor tissue and (c), HEI-193 cells. The arrow bars point the peaks present in the blood DNA, but were missing in the tumor tissue and culture cells. To examine any large fragment of intra-chromosomal deletion, the same kind of LOH analysis for chromosome 17 was also performed with the DNA from (d), blood; (e), tumor tissue; and (e, HEI-193 cell line. No significant loss of heterozygosity was observed on chromosome 17 except total loss of second chromosome 17 was demonstrated in FIG. 6.
Figure 7E:
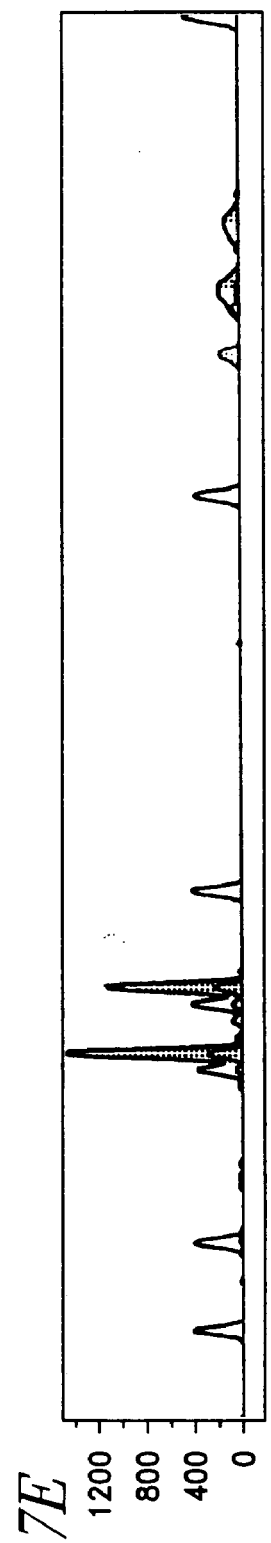
Figure 7F:
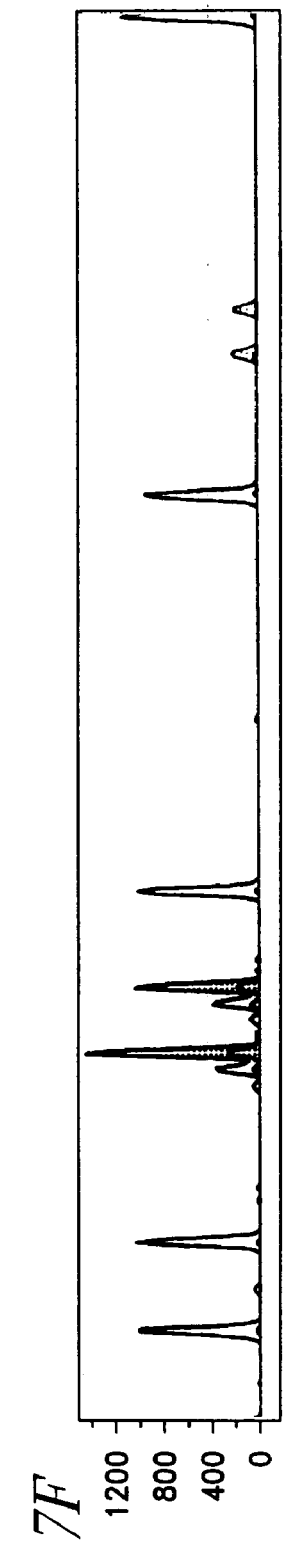

Genomic DNAs were extracted from primary culture cells and cell line HEI-193 at Passage 6 and 9 and compared with DNA from the peripheral blood cells as well as tumor tissue. LOH analysis using microsatellite markers flanking or within the NF2 gene revealed loss of some parts of NF2 allele in tumor tissue and cultured cells, but not in blood cells. In the blood sample, the heterozygosity showed two peaks for each of the markers: D22S430 (Peak 79, 87), NF2CA3 (Peak 131, 133), D22S275 (Peak 161,167), CRYB (Peak 173, 175) and D22S268 (Peak 196, 206). In contrast, the DNAs from either tumor tissue or the HEI-193 cell line showed only one heterozygosity peak out of two in each marker (FIG. 7, a, b and c). This suggested that the second somatic mutation in tumor cells is either large deletion on the trans chromosome or loss the entire copy of chromosome 22.

Example 8

Tumorigenicity in Mouse

No sign of tumor growth was observed in either SCID (n=2) or nude mice (n=2) during the 8 weeks post-inoculation of schwannoma cell line.

By using retroviral mediated gene transfer technique, we have described the establishment of vestibular schwannoma from neurofibmma type two (NF2) patient with a unique NF2 gene splice site mutation. The clinical manifestations of this patient were typically a mild phenotype. According to our knowledge, there is no report on the successful establishment of a human schwannoma cell line. Until recently, because of the availability of a Schwann cell growth factor, heregulin, our laboratory and others (Pelton, P. D. et at. 1998 *Oncogene* 17:2195-2209; Hung, G. et al. 1999 *Int J Oncogene* 14:409-15; Rosenbaum, C. et al. 1998 *Neurobiol Dis* 5:55-64; Hanemann, C. O. et al. 1998 *Glia* 22:89-98) have used a similar method for establishing short-term primary schwannoma cells in culture. The ideal in vitro system to study NF2 at the cellular and molecular level and to test therapeutic approaches is primary cell culture because it most represents in vivo characteristics. However, most of the surgical specimens are usually too small for sufficient cell numbers, and once the tissue cells grow in culture they usually stop proliferation in early passages, even cultured in the chemical defined medium which subsidizes several Schwann cell growth factors and mitogens such as insulin, heregulin and forskolin. There may exist some key factors which could keep the culture cells proliferating and which have not yet been identified. In addition, primary culture cells are polyclonal and more or less contaminated with other stroma cells. All of these factors may affect both the quality and reproducibility of research. Establishing stable immortalized Schwann and schwannoma cell lines is essential.

We immortalized vestibular schwannoma cells from a primary Schwann cell culture. We have chosen a retroviral mediated gene transfer technique to deliver the immortalization agent. Retrovirus has relatively higher transduction efficiency than non-viral carriers, and most importantly the retrovirus can stably integrate into the target cell genome. Human -papilloma virus type 16 E6 and E7 genes are considered as oncogenes which have been found associated directly with cervical cancer in women (Laimins, L. A. 1993 *Infect Agents Dis* 2:74-86). It is found that at molecular level the E6/E7 gene products interfere with the function of tumor-suppressor protein p53 and Rb (Retinoblastoma), respectively, thereby preventing cell cycle arrest without causing significant transformation (Band, V. et al. *EMBO J* 12:1847-52; Demers, G. W. et al. 1994 *PNAS USA* 91:4382-6). Transduction of either E6 or E7 gene alone can prolong the primary culture life by inducing hyperproliferation, but has very low frequency of transduction in primary cells. However, by co-expression of E6 and E7 genes, we can substantially increase the immortalization events (Hawley-Nelson, P. et al. 1989 *EMBO J* 8:3905-3910; Coursen, J. D. et al. 1997 *Exp Cell Res* 235: 245-253).

In general, a two-stage model of mortality stage 1 (M1) and mortality stage 2 (M2) is involved during immortalization process (Coursen, J. D. et al. 1997 *Exp Cell Res* 235:245-253). The M1 leads to cellular senescence, when normal cells have reached the end of their proliferation capacity. Expression of HPV E6/E7 proteins can help cells overcome M1. Escape from M1 results in an expanded in vitro life span during which the cells continue to proliferate until M2. At this point most cells enter crisis. Eventually, some cells gain additional genetic alteration that allows them to survive at M2 and have ability to proliferate indefinitely (e.g., immortalization). The same phenomena have been recently reported when using HPV E6/E7 to immortalize human bronchial epithelial cells (Coursen, J. D. et al. 1997 *Exp Cell Res* 235:245-253). In our hand, we have observed two major phenotypic changes during the immortalization process. The first phase is between Passage 1 and Passage 14. Between Passage 1 and 7, the increasing proliferation rate and life span were observed in culture. M1 began at Passage 7 and reached its peak at Passage 14, at which time cells exhibited increasing heterogeneity in shape and cell death. A population of cells formed syncytia, which is believed the signal of cell death (Hung, G. et at. 1999 *Int J Oncogene* 14:409-15). By the second phase, at Passage 15, a population of cells had gone through the crisis and survived to become immortalized. By comparing the genotyping data from primary culture cells at Passage 6 and 9 with the blood and the tumor tissue, no sign of LOH in chromosome 17 was observed (FIG. 5, d, e, f). But when the cells were karyotyped at Passage 17, loss of one copy of chromosome 17 in addition to other monosomies, chromatid gaps and breaks and aberrant chromosome has been observed (FIG. 6). Similar high genomic instability and telomerase activity have also been seen in human bronchial epithelial cell immortalization by E6 and E7 genes (Coursen, J. D. et at. 1997 *Exp Cell Res* 235:245-253).

The Schwann cell origin of the immortalized cells was confirmed by the presence of Schwann cell marker S100 (FIG. 4). Although the immortalized culture is still a pool of transformed cells, RT-PCR has confirmed no wild type NF2 gene transcripts were detected (FIG. 4) from the cells. Furthermore, loss of polymorphic marker or of whole copy of chromosome 22 was observed in cytogenefic data, suggests that this tumor has a splice site point gemline mutation. The immortalized schwannoma cells have increased population doubling rate, high saturation density and altered expression of S100. However, the genetic situation at the current passage still does not complete the requirement of tumorigenicity in animal. Continuous proliferation of immortalized cells may accumulate further genetic alterations, which may eventually transform the cells to be completely tumorigenic.

In conclusion, our results demonstrate for the first time that it is possible to establish a human schwannoma cell line by immortalization with a retrovirus construct containing human papilloma virus E6/E7 genes. This immortalized schwannoma cell line, HEI-193, is stable and nonmalignant with Schwann cell origin and NF2 gene mutation. This cell line is envisioned to be very useful for studying NF2 gene function, genotype-phenotype correlation of NF2, mutagenesis and tumorigenicity of schwannoma cells. In addition, it is envisioned as an in vitro model for testing therapeutic approaches.

This work was supported by House Ear Institute internal fund US Army Grant DAMD17-99-1-9491.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. An isolated HEI-193 human schwannoma cell line actively expressing the E6 and E7 genes of human papilloma virus 16 deposited as ATCC Accession #PTA-4544, wherein said cell line has a mutant NF2 gene and the phenotypic characteristics comprising rapid growth, and antigen-positive for S100.

2. A method for determining an effect of a pharmacological agent on the isolated HEI-193 human schwannoma cell line of claim 1, said method comprising:
   a) contacting said cell line with said pharmacological agent; and
   b) determining the effect of said pharmacological agent on said cell line.

3. The method of claim 2, wherein the effect is a change in cell growth.

4. The method of claim 2, wherein the effect is a change in a phenotypic characteristic of the cell line.

5. The method of claim 4, wherein the change is an increase or decrease in expression of a cellular gene.

6. The method of claim 5, wherein the cellular gene expresses a gene product selected from the group consisting of: cell cycle proteins, transcription factors, signaling molecules, cytokines, growth factors, and growth factor receptors.

7. The method of claim 2, wherein the pharmacological agent is selected from the group consisting of chemicals, drugs, hormones, cytokines, and growth factors.

8. The method of claim 2, wherein said effect is selected from the group consisting of: genotoxicity, DNA adduct formation, mutagenicity, cell transformation and/or cytotoxicity, programmed cell death, chromosomal damage, de-myelination, and remyelination.

* * * * *